United States Patent [19]

Vuylsteke

[11] Patent Number: 5,684,888
[45] Date of Patent: Nov. 4, 1997

[54] METHOD OF MONITORING THE SENSITIVITY OF A SYSTEM FOR READING A RADIATION IMAGE STORED IN A PHOTOSTIMULABLE PHOSPHOR SCREEN

[75] Inventor: Pieter Vuylsteke, Mortsel, Belgium

[73] Assignee: Agfa-Gevaert, Mortsel, Belgium

[21] Appl. No.: 286,483

[22] Filed: Aug. 5, 1994

[30] Foreign Application Priority Data

Aug. 16, 1993 [EP] European Pat. Off. .............. 93202389

[51] Int. Cl.$^6$ ........................................ G06K 9/00
[52] U.S. Cl. ........................ 382/128; 382/132; 382/172
[58] Field of Search ............................ 382/128, 132, 382/270, 272, 254, 131, 168, 169, 170, 171, 172, 190, 195, 199, 271, 273, 274, 275, 309, 311, 318, 319

[56] References Cited

U.S. PATENT DOCUMENTS

| | | | |
|---|---|---|---|
| 4,851,984 | 7/1989 | Doi et al. | 382/132 |
| 5,172,419 | 12/1992 | Manian | 382/132 |
| 5,198,669 | 3/1993 | Namiki et al. | 382/132 |
| 5,221,843 | 6/1993 | Alvarez | 250/327.2 |
| 5,297,036 | 3/1994 | Grimaud | 382/132 |
| 5,309,237 | 5/1994 | Singh | 348/607 |
| 5,319,696 | 6/1994 | Abdel-Malek et al. | 378/108 |

FOREIGN PATENT DOCUMENTS

| | | | |
|---|---|---|---|
| A-0280 412 | 8/1988 | European Pat. Off. | G06F 15/68 |
| A-2293 011 | 6/1973 | France | G06F 15/34 |
| A-57 028 275 | 5/1982 | Japan | G06F 15/68 |

*Primary Examiner*—Jose L. Couso
*Assistant Examiner*—Matthew C. Bella
*Attorney, Agent, or Firm*—Richard J. Birch

[57] ABSTRACT

A method for monitoring the sensitivity of a system that reads a radiation image or an irradiated object with the radiation image being stored in a photostimulable phosphor screen. The method employs the steps of scanning the screen with stimulating irradiation, detecting the light emitted upon stimulation, compressing the electric representation through square root amplification, and then digitizing the compressed electric representation. For a sensitivity class that was set when the radiation image was generated a corresponding expected noise variance value $\sigma_e^2$ is retrieved from a predefined table and the ratio $\sigma_y^2/\sigma_e^2$ is calculated and thresholded. A warning is generated when the ratio exceeds a threshold value $T_+$ or when the ratio is smaller than a threshold value T.

12 Claims, 8 Drawing Sheets

| sensitivity class | PM voltage (V) |
|---|---|
| 25 | 541 |
| 50 | 596 |
| 100 | 657 |
| 200 | 725 |
| 400 | 799 |
| 800 | 881 |

| sensitivity | $\sigma_e^2$ |
|---|---|
| 25 | 19 |
| 50 | 38 |
| 100 | 75 |
| 200 | 150 |
| 400 | 300 |
| 800 | 600 |

METHOD OF MONITORING THE SENSITIVITY OF A SYSTEM FOR READING A RADIATION IMAGE STORED IN A PHOTOSTIMULABLE PHOSPHOR SCREEN

BACKGROUND OF THE INVENTION

1. Field of the Invention

The invention is in the field of digital radiography. The invention more specifically relates to a method of monitoring the sensitivity of a system for reading a radiation image that has been stored in a photostimulable phosphor screen.

2. Description of the Prior Art

In digital radiography a technique has been developed wherein a radiation image of an object is obtained by using a screen comprising a photostimulable phosphor such as described in European patent application 503 702 published on 16 Sep. 1992 now granted and in U.S. Ser. No. 7/842,603 now U.S. Pat. No. 5,340,661.

Upon exposure to penetrating radiation such as x-rays emitted by a radiation source, a photostimulable phosphor screen of the kind described in the above patent applications stores energy. The stored energy can be released by scanning the screen with stimulating radiation, e.g. laser light of the appropriate wavelength. The light emitted upon stimulation which is proportional to the original incident radiation absorption in the screen can then be detected and converted into an electric representation by a detector such as a photomultiplier. The read out signal is then digitized.

Preferably the analog image signal is compressed by means of a square root amplifier before being fed to an analog to digital convertor. Compression according to a square root characteristic is advantageous in that it provides optimal use of the dynamic range of the A/D convertor. The result of a compression according to square root characteristic has a constant noise level throughout the compressed signal range. Since the quantisation error is also constant, the ratio of quantisation noise to signal noise is also constant resulting in an optimal distribution of the bits throughout the dynamic range of the A/D convertor.

After A/D conversion one disposes of an N-bit 'raw' image signal, that can be subjected to image processing before hard copy recording or display so that for each type of examination the diagnostically relevant information can be reproduced in optimal conditions.

Among the image processing algorithms a so-called autowindowing algorithm can be applied to determine the diagnostically relevant signal range out of the entire read out signal range.

The latitude and position of this relevant range can be determined automatically using significant points (minima, maxima . . . ) of the image histogram. A method of determining such significant points has been described in our European application EP 546 600 now granted.

The data within the selected window are then mapped onto the density range available on a recording material or on a display. One embodiment of such a signal-to-density mapping method is described in our European application EP 549 009 now granted and in U.S. Ser. No. 07/978,091 now U.S. Pat. No. 5,333,065.

The conversion of signal values into corresponding density values is no longer limited by the properties of the recording material, a virtually unlimited number of signal-to-density transformations (or "sensitometries") adapted to each specific application can be selected.

With optimal window-level settings and selection of optimal reproduction sensitometry, it is in most circumstances possible to obtain high quality reproductions.

Hence the image processing provides that a diagnostically relevant signal range is extracted from the total signal range and that this extracted signal range is optimally mapped onto an available density range in the hard copy.

The image processing algorithms also provide that in case of a drift of the overall sensitivity of the read-out system, resulting in a shift of the image signal range on the logarithmic signal axis, still good reproductions will be obtained since the relevant signal range will automatically be extracted and will be optimally mapped onto the available density range.

From the outlook of the reproduction or the display of the image no deterioration of the sensitivity of the read out system that may be due to deviations of the optic elements, of the laser power, of the characteristic of the amplification, of the characteristics of the analog-to-digital conversion etc. will be deducible.

By evaluating the position of the image histogram relative to the signal axis, the radiologist might get feedback on the position of the relevant data range relative to the entire data acquisition range and might conclude that a drift of the sensitivity of the system had occurred.

However, when detecting that the position of the image histogram does not match with the expected position this does not unambiguously give an indication on the underlying cause: the deviation might originate from a drift of the sensitivity but other causes such as a deviation of the actually applied irradiation dose from the set irradiation dose may also result in a shift of the signal range on the signal axis. This latter cause will also be eliminated by adequate image processing and will not be visible in the reproduction or display.

SUMMARY OF THE INVENTION

Objects of the invention

It is an object of the invention to provide a method of monitoring the sensitivity of a system for reading a radiation image that has been stored in a photostimulable phosphor screen and wherein the image is read out by scanning said screen with stimulating rays and detecting the light emitted upon stimulation.

It is a further object to provide such a method wherein the system's sensitivity is controlled without being affected by other system parameters or adjustments.

It is a further object of this invention to provide an apparatus for carrying out the above method.

Still further objects will become apparent from the description hereinbelow.

Statement of the invention

The above objects are accomplished according to this invention by a method of monitoring the sensitivity of a system for reading a radiation image of an object that has been exposed to irradiation, said radiation image having been stored in a photostimulable phosphor screen, comprising the steps of scanning said screen with stimulating irradiation, detecting the light emitted upon stimulation, converting the detected light into an electric representation, compressing said electric representation through square root amplification, digitizing the compressed electric representation, selecting for a sensitivity class that was set when said radiation image was generated a corresponding expected noise variance value $\sigma_e^2$ from a table which comprises for a number of predefined sensitivity classes corresponding noise variance values, each of said corresponding noise variance values representing the average variance of noise present in an image read out with said system being calibrated for the corresponding sensitivity class, computing for the read out image the effective noise variance $\sigma_y^2$, calculating the ratio $\sigma_y^2/\sigma_e^2$, thresholding said ratio, generating a warning at least in one of the cases wherein said ratio exceeds a threshold value $T_+$ and wherein said ratio is smaller than some threshold value $T_{31}$.

DETAILED DESCRIPTION OF THE INVENTION

The present invention is based on the inventor's acknowledgement that the sensitivity of the read-out system can be monitored by evaluation of the variance of the noise of a read out image and that by monitoring the system's sensitivity by means of the noise variance the influence of the irradiation dose is eliminated.

Indeed, when defining s as the number of photons detected by the detector of the read out system, for example a photomultiplier, in case of no object attenuation (attenuation factor a equal to 1), and x as the number of photons detected by the detector with attenuation a, then x is equal to the product of s and a.

Assuming that the statistical distribution of the number of photons detected by the photomultiplier is a Poisson distribution, then $$\sigma_x = x^{1/2} = (s.a)^{1/2};$$

This assumption is correct as long as the irradiation doses are not extremely high, typically this assumption holds for irradiation amounts expressed as sensitivity classes (definition explained furtheron within the range of 25 to 800).

When the read out system has a sensitivity G and signal values are converted by the read out system to square root E (E representing 'exposure') values, then $$y = (G.x)^{1/2} = (G.s.a)^{1/2}$$

wherein y represents the digital signal per pixel, and $$\sigma_y = y'(x).\sigma_x = (G)^{1/2}.(2(x)^{1/2})^{-1}.\sigma_x = (G)^{1/2}/2.$$

So, the effective sensitivity of the read-out system can be determined as $4\sigma_y^2$, wherein $\sigma_y^2$ is the noise variance of pixel values read out from an exposed phosphor screen and subjected to square root amplification.

Thus, the sensitivity of the read out system can be monitored by evaluating the value $\sigma_y^2$.

The ratio $\sigma_y^2/\sigma_e^2$ determined in the method of the present invention expresses a relative sensitivity error.

Sensitivity class:

In classical radiography wherein a radiation image is recorded onto a radiographic film, a relation has been established which defines for each specific radiographic film the optimal radiation dose to be applied in order to achieve that the diagnostically relevant part of an image is reproduced on the radiographic film at an optimal image density.

Different types of radiographic films have been developed that each provide this optimal reproduction at different irradiations doses. Each of these different types of films is particularly suitable for a specific examination or group of examinations.

The radiation dose suitable for application with a specific radiographic film is defined by a value S which is a characteristic of a given radiographic film called the "speed class" of the film. For each radiographic film the optimal irradiation dose can be deduced from the speed class value by applying the formula given hereinbelow.

When setting the radiation dose at the deduced value, the diagnostically relevant part of an image will be recorded on a selected film at an optical density which is approximately 1.0 above fog and base density.

This speed class value S is defined as follows:

$$S = \frac{10^{-3} \, Gy}{K_s}$$

wherein $K_s$ represents the exposure dose required to produce on said film an optical density of 1.00 above fog and base density, said value $K_s$ being expressed in Gy.

For example, when using a class 100 film for recording a radiation image, the x-ray dose must be adjusted so that the average dose at the detector (so at the radiographic film) is about $10^{-5}$ Gy in the regions of diagnostical interest which corresponds to an exposure dose of 1.14 mR; when using a film of speed class 200 the dose can be halved etc.

It is common practice to quantify the applied radiation dose by means of the corresponding speed class of the film which is suited for that specific dose.

Exposure of a photostimulable phosphor screen instead of a film of a specific speed class is performed by applying the same radiation dose as would be appropriate for a film of said specific speed class.

Following exposure the image stored in the exposed photostimulable phosphor screen is read by scanning said screen with stimulating radiation (such as laser light of the appropriate wavelength) and by detecting the light emitted upon stimulation by means of a detector.

In a practical embodiment the detector is a photomultiplier with an adjustable photomultiplier voltage, which allows for changing the sensitivity of the read out system.

Unlike conventional radiography where films of different speed classes are used to match the applied radiation dose, it is sufficient in a digital read out system to switch the system's sensitivity to a suitable value, in accordance with the applied radiation dose. In a preferred embodiment the selection of the sensitivity class is done stepwise, each of the steps for example differing by a factor two.

Each setting of the photomultiplier is associated with 'a sensitivity class' in analogy with the notion of 'speed classes' used in connection with conventional radiographic film.

Calibrated system:

The method of the present invention implies the use of a so-called calibrated system.

A read out system is said to be 'calibrated for a given sensitivity class' if the sensitivity of the detector of said read out system is adjusted so that the mean signal value read out of a screen that has been exposed to an amount of irradiation suitable for a given sensitivity class is equal to a predefined value $y_e$.

This is accomplished by adjusting the photomultiplier voltage with a value retrieved from a table which contains the appropriate photomultiplier voltage for each selectable sensitivity class.

The photomultiplier voltage associated with each sensitivity class entry in the table is determined iteratively as follows:

(1) uniformly exposing an image plate with the radiation dose suited for said sensitivity class, (2) reading out the image plate and determining the mean signal value $y_m$.

These iterations are stopped if y is sufficiently close to the desired value $y_e$; otherwise the photomultiplier voltage is raised or lowered depending on whether y was smaller or greater than $y_e$, and steps 1 and 2 are repeated.

The predefined value $y_e$ is typically chosen to be in the center of the dynamic range of the system, so that there is sufficient margin for under- and overexposure.

Thresholding and output:

The thresholding used in the method of the present invention can be implemented in various ways.

In one embodiment the ratio $\sigma_y^2/\sigma_e^2$ is compared with two threshold levels indicated by $T_-$ and $T_+$.

In case the ratio $\sigma_y^2/\sigma_e^2$ exceeds some predetermined threshold $T_+$ an output warning (e.g. in the form of a visual or an auditive warning) is generated informing the operator of the read out apparatus that the system's sensitivity is too high; likewise in case the above ratio is smaller than $T_-$ a warning can be generated informing the operator that the system's sensitivity is too low.

The threshold values are determined so that small variations due to limited measurement precision and normal sensitivity fluctuations are not exceeding threshold, typically $T_-=0.75$ and $T_+=1.25$.

An output can also be generated of the relative sensitivity error $\sigma_y^2/\sigma_e^2$ or of the logarithm thereof. This output can be generated on a screen of a monitor or on the keypath of the apparatus or can be written into an electronic log file or can be recorded on film accompanied by the read out image.

In an alternative embodiment of the present invention the ratio $\sigma_y^2/\sigma_e^2$ can be computed for a number of N images (for example N last successively read out images) and the average value of the ratios computed for each of these N images can be calculated and can be subjected to a similar thresholding operation as provided in case of a single image.

Still alternatively this ratio can be calculated for N images (for example N last read out images), and the values can then be subjected to linear regression instead of being subjected to averaging.

The thresholding can then be applied to the absolute value of the slope of the regression line, in case the absolute value of the slope of this regression line exceeds some threshold value $T_r$ a warning can be generated for the operator that there is a gradual degradation of the system's sensitivity.

It will be clear that it is the task of the operator to react on the generation of a warning signal by further evaluating the components of the read out system so as to detect the cause of the sensitivity change (sensitivity too high or too low) and to adjust the sensitivity in order to obtain an envisioned sensitivity value.

Noise variance:

The method of the present invention comprises calculation of the noise variance. An example of a methods of calculating the noise variance will be described hereinbelow with reference to the drawings.

The described method is preferred especially in cases wherein a pyramidal decomposed image representation is available for example because it has already been calculated during the image processing cycle for other purposes such as contrast enhancing image processing, or noise reducing image processing etc.

The invention further relates to an apparatus for carrying out the method of the present invention. The apparatus comprises means for scanning said screen with stimulating irradiation, read out means for detecting light emitted upon stimulation and for converting said light into an electric signal representation, amplifying means having a square root characteristic for amplifying said signal representation, means for storing a table which comprises for a number of predefined sensitivity class settings corresponding noise values $\sigma^2_{e,i}$, each of said noise variance values representing the average variance of noise present in an image read out with read out means being calibrated for the corresponding sensitivity class, means for retrieving from said table for a given sensitivity class the corresponding noise value $\sigma^2_e$, means for calibrating said read out means for a specific sensitivity class, means for reading an image stored in a screen, means for computing for said read out image the effective noise variance $\sigma^2_y$, means for calculating the ratio $\sigma_y^2/\sigma_e^2$, means for thresholding said ratio, means for generating a warning at least in one of the cases wherein said ratio exceeds a threshold value $T_+$ and wherein said ratio is smaller than some threshold value $T_-$.

The apparatus can also be provided with means for outputting said ratio (or the logarithm thereof) or the result of said thresholding.

BRIEF DESCRIPTION OF THE DRAWINGS

Further details concerning the method of the present invention and the above apparatus will be explained hereinbelow with reference to the drawings, wherein FIG. 1 generally shows a system in which the method of the invention can be applied.

Figure 1:
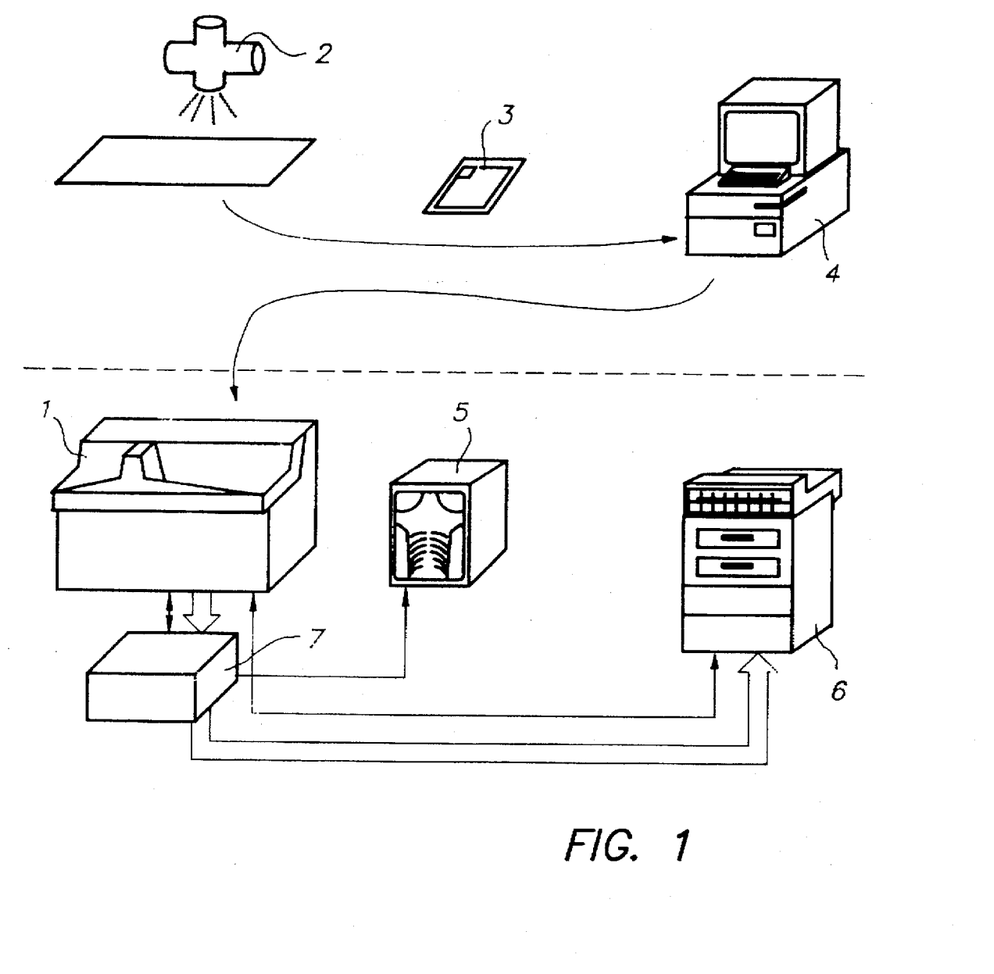

FIG. 1 generally shows an apparatus in which the method of the invention can be applied.

A radiation image of an object was recorded on a photostimulable phosphor screen (3) by exposing (2) said screen to x-rays emitted by a source of irradiation and transmitted through the object (not shown).

The adjustment of the source of irradiation was performed by calculating for a specific speed class the appropriate amount of irradiation and by adjusting the source so as to (at least theoretically) produce said amount.

The stimulable phosphor screen was conveyed in a cassette (3) provided with an electrically erasable programmable read only memory (EEPROM). In an identification station (4) various kinds of data, for example patient identification data (name, date of birth) and data relating to the exposure such as the sensitivity class setting and data relating to the examination type or to the expected diagnosis were written into the EEPROM.

Figure 2:
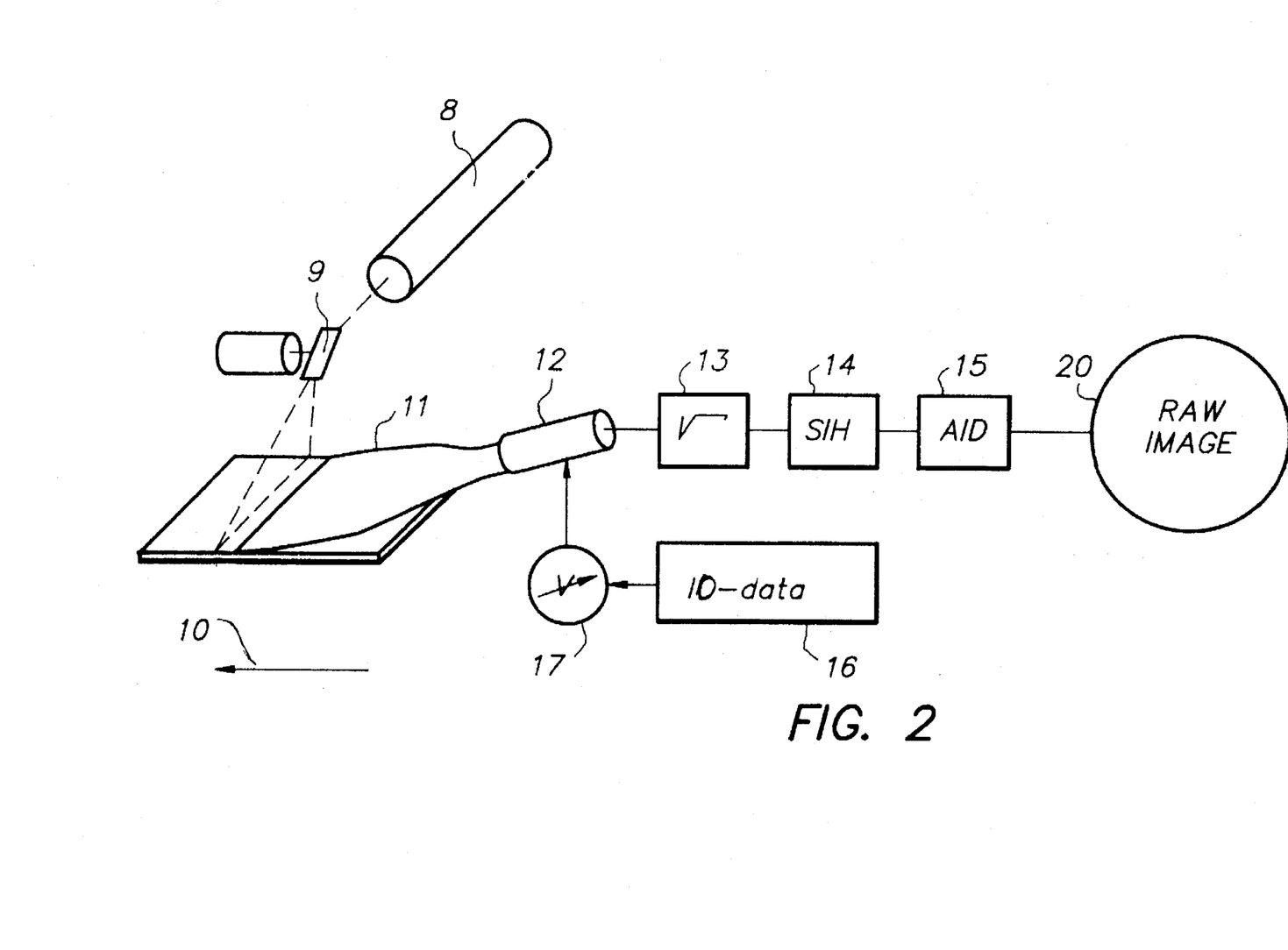
FIG. 2 is a specific embodiment of an apparatus for reading out an image stored in a photostimulable phosphor screen.

The operation of radiation image read-out apparatus 1 is illustrated in FIG. 2.

First the data stored in the EEPROM were read out (not shown).

The value representing the selected speed class (16) was used to preset the sensitivity of the photomultiplier by adjusting (17) its cathode voltage to a value retrieved from a table that comprises for a number of sensitivity class settings of said read out apparatus corresponding adjustment values for the photomultiplier voltage.

The adjustment values were determined in advance following the procedure described furtheron and stored in the form of a look up table in a memory part of the read out apparatus (1).

The cathode voltage values for the photomultiplier are such that the mean signal value read out of a screen that has been exposed to an amount of irradiation by means of said read out means being adjusted by the corresponding value is equal to an expected value $y_e$.

The adjustment values stored in a look up table were determined by an iterative process wherein first an exposure is made according to a specific sensitivity class, then the signal $y_a$ is detected by means of a photomultiplier the cathode voltage of which is set to an initial value. Next, the photomultiplier cathode voltage is adjusted if the detected signal is too low or too high and the procedure of exposing, detecting and adapting the photomultiplier voltage is repeated until $y_a$ equals $y_e$.

The above steps are repeated for every entry (exposure class) in the table.

Figure 3:
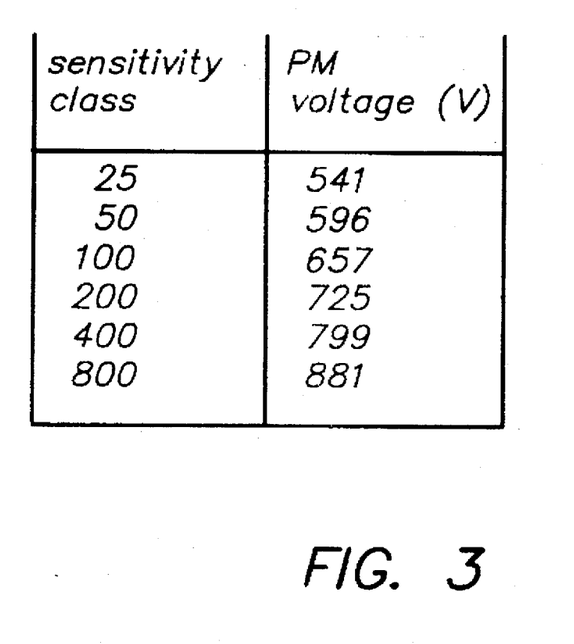
FIG. 3 is a look up table relating sensitivity class values with corresponding adjustment values for the cathode voltage of the photomultiplier.

An example of such a look up table is illustrated in FIG. 3.

The sensitivity class setting was further used together with the data regarding the particular application to control the selection of the parameters for the image processing, referred to hereinbelow.

Next, the radiation image stored in the photostimulable phosphor screen was read-out by scanning the phosphor screen with stimulating rays emitted by a laser (8). The stimulating rays were deflected according to the main scanning direction by means of galvanometric deflection device (9). The secondary scanning motion was performed by transporting the phosphor screen in a direction indicated by arrow (10) perpendicular to the main scanning direction. The stimulated emission was directed by means of light collector (11) onto a photomultiplier (12). A cylindrical mirror (not shown) was provided for directing the light emitted upon stimulation into the entrance face of the light collector (11). The light directed onto photomultiplier (12) was converted into an electric signal representation. This signal was thereupon amplified in an amplifier (13) having a square root characteristic and sampled by a sample and hold circuit (14). Then it was convened into a 12 bit digital signal by means of an analog to digital converter (15).

After read-out the photostimulable phosphor screen was conveyed through an erasure section (part of read out apparatus (1)) for erasing any residual image remaining on the photostimulable phosphor screen. The erasing section comprises a number of aligned quartz tungsten halogen lamps with a continuous spectral irradiance output distribution extending approximately from 0.2 micrometer to 2.5 micrometer.

Figure 4:
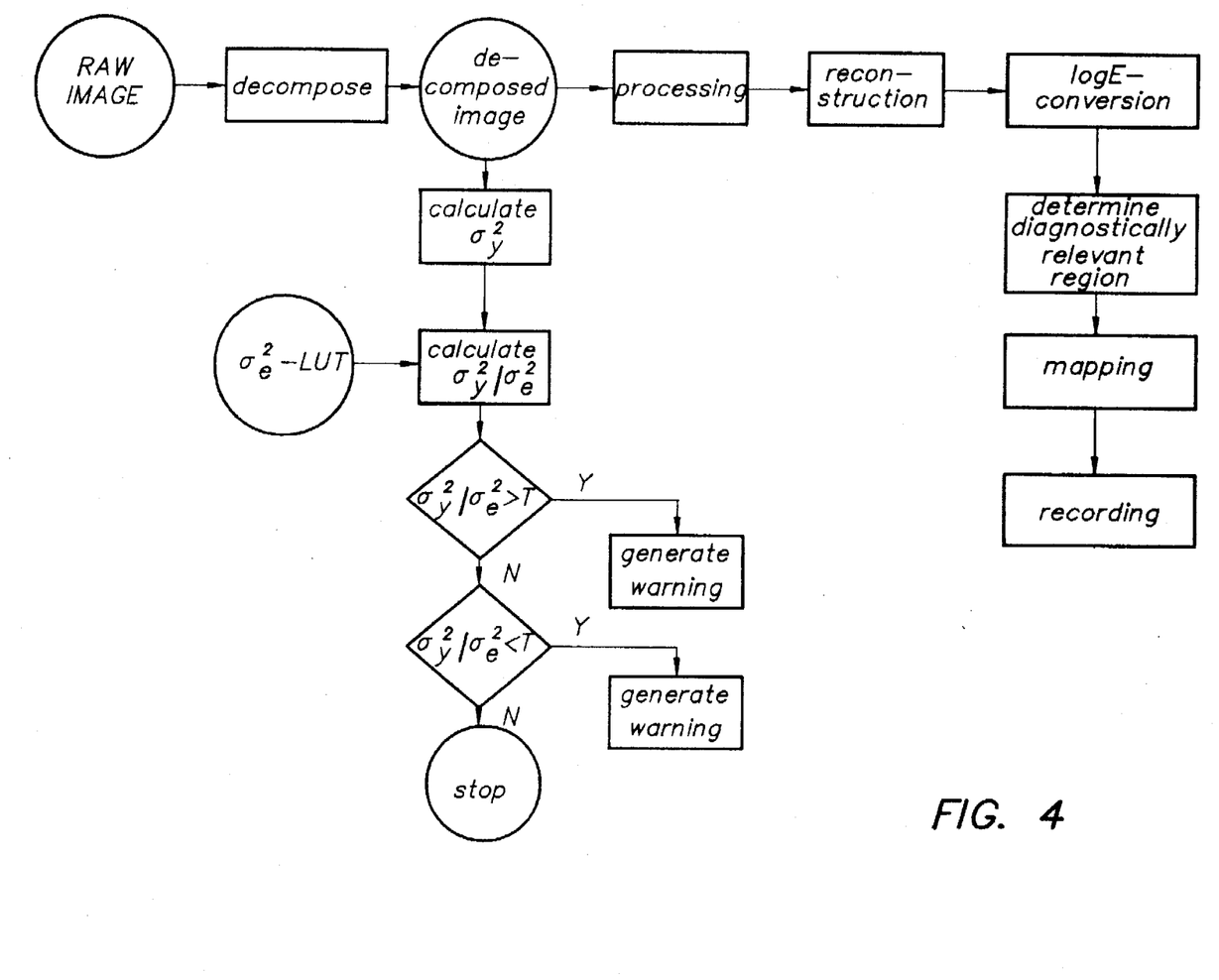
FIG. 4 illustrates the data flow.

The subsequent data flow is illustrated in FIG. 4.

The digital image signal, called the 'raw' image or 'original' image (20) was sent to the image processing module of the read-out apparatus (FIG. 1, numeral 7).

The processing performed in the image processing module was based on a pyramidal decomposition of the image signal into detail images at multiple resolution levels and a residual image.

The detail images are modified and the modified detail images and the residual image are recombined by application of a reconstruction algorithm to obtain a processed image representation that is finally converted into a visible image (display or hard copy).

The decomposition of an image into a sequence of detail images at multiple resolution levels and a residual image as well as image processing on the basis of a multiresolution image representation has been described in extenso in our European patent application 527.525 filed Aug. 14, 1991 and in our European patent application 93200375.9 filed Feb. 11, 1993.

Figure 5:
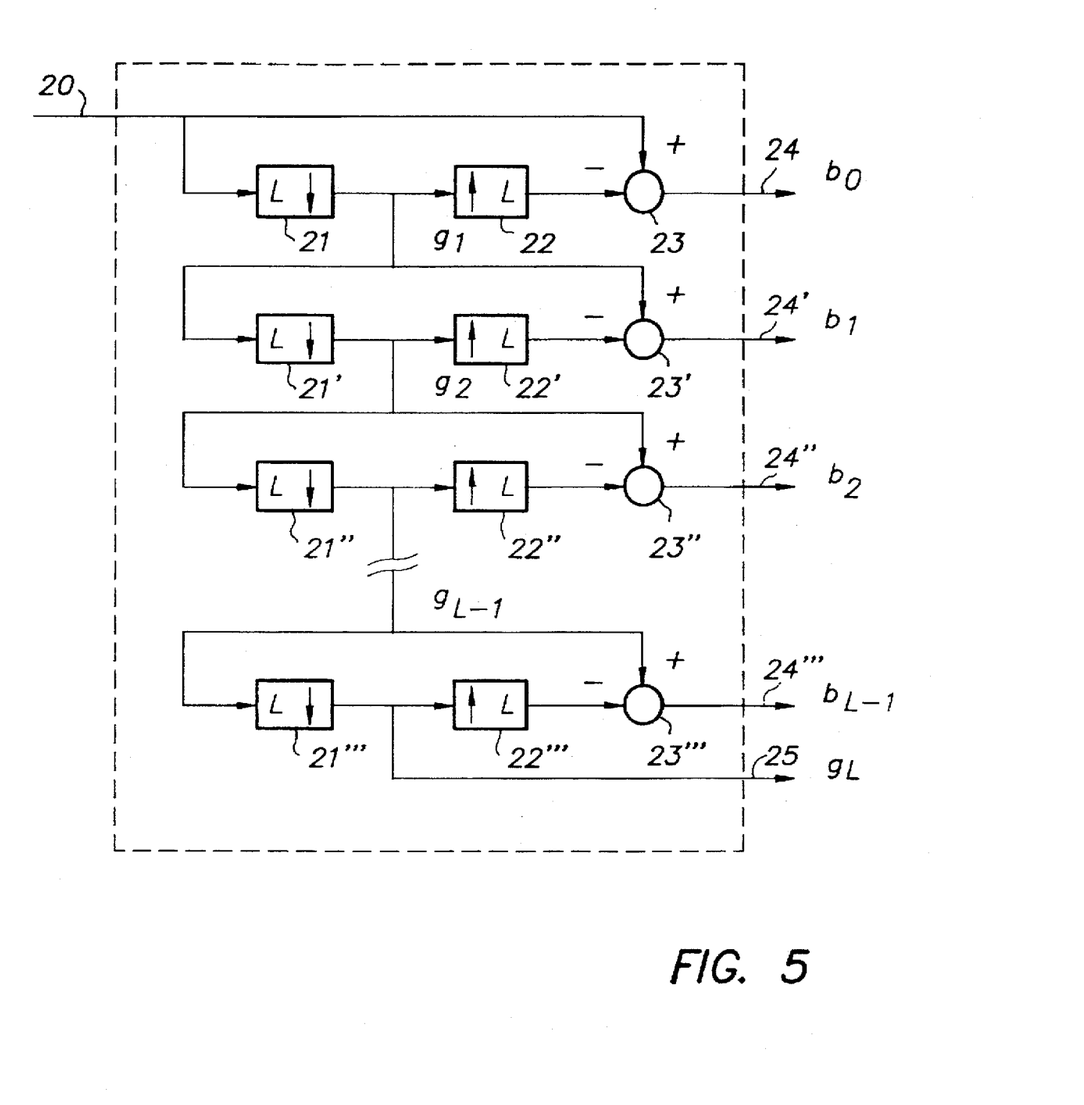
FIG. 5 is a device for performing pyramidal image decomposition.

One embodiment of the decomposition process is depicted in FIG. 5. In the decomposition section the original image 20 is filtered by means of a low pass filter 21, and subsampled by a factor of two, which is implemented by computing the resulting low resolution approximation image $g_1$ only at every other pixel position of every alternate row. A detail image $b_0$ at the finest level is obtained by interpolating the low resolution approximation $g_1$ with doubling of the number of rows and columns, and pixelwise subtracting the interpolated image from the original image.

The interpolation is effectuated by the interpolator 22, which inserts a column of zero values every other column, and a row of zero values every other row respectively, and next convolves the extended image with a low pass filter. The subtraction is done by the adder 23.

The same process is repeated on the low resolution approximation $g_1$ instead of the original image, yielding an approximation of still lower resolution $g_2$ and a detail image $b_1$.

A sequence of detail images $b_i$, i=0 ... L−1 and a residual low resolution approximation $g_L$ are obtained by iterating the above process L times.

The finest detail image $b_0$ has the same size as the original image. The next coarser detail image $b_1$ has only half as many rows and columns as the first detail image $b_0$. At each step of the iteration the maximal spatial frequency of the resulting detail image is only half that of the previous finer detail image, and also the number of columns and rows is halved, in accordance with the Nyquist criterion. After the last iteration a residual image $g_L$ is left which can be considered to be a very low resolution approximation of the original image. In the extreme case it consists of only 1 pixel which represents the average value of the original image.

The decomposed image can be subjected to various kinds of processing implemented by modifying the detail images according to a specific transformation.

Examples of image processing methods can be found in the following European applications:

EP 527.525; EP 574.969 and in 93200375.9 filed Feb. 11, 1993.

It will be clear to the man skilled in the art that the image can be subjected to a wide variety of image processing algorithms for contrast enhancement, noise reduction and several other purposes before being applied to the recorder or to the display device for reproduction or display.

The type of image processing as well as the parameters to be used when processing the image can be defined by means of information that was written into the EEPROM provided on the screen conveying cassette.

Processing parameters can for example be retrieved from a prestored look up table in correspondence with a specific type of examination that has been entered into the EEPROM during identification.

Alternatively the type of processing as well as the parameters to be used can be selected (and for example retrieved from a look up table) in dependence on the expected diagnosis.

Figure 6:
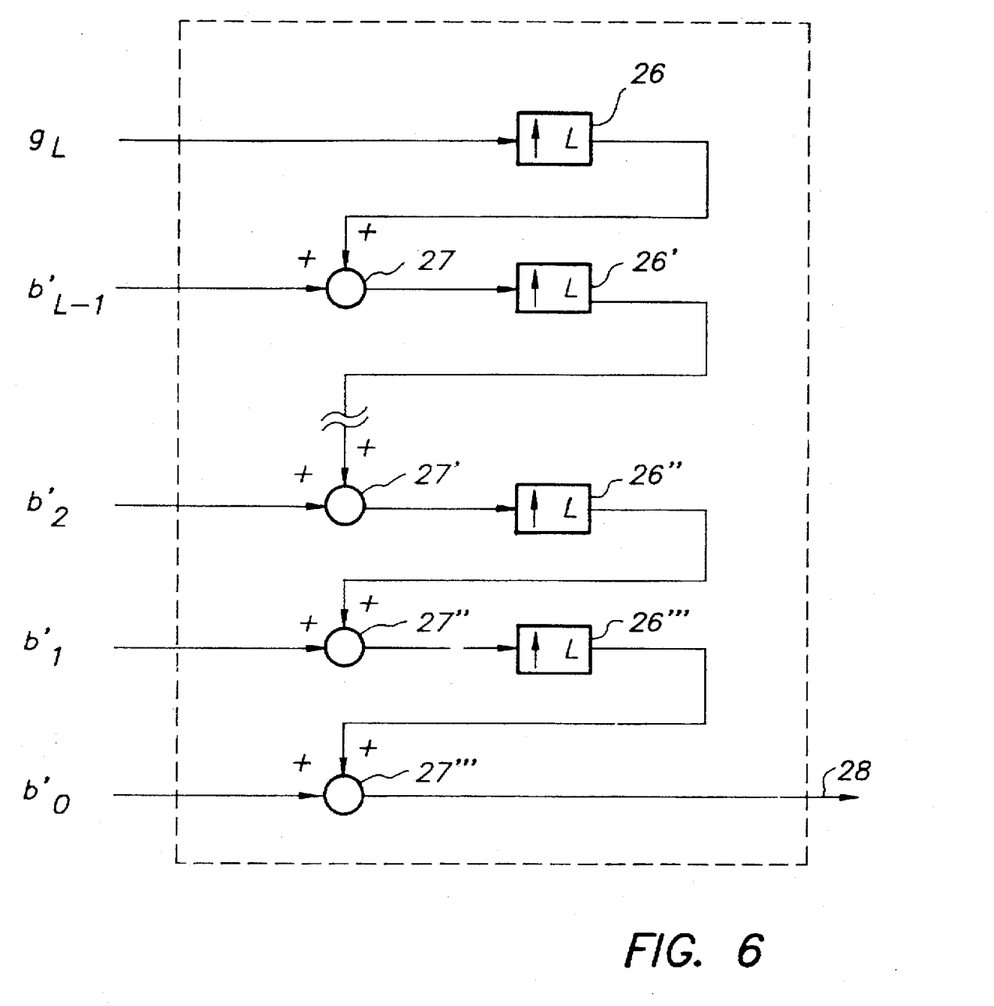
FIG. 6 is a device for performing reconstruction of a processed image.

A processing cycle applied to a decomposed image signal is terminated with reconstruction of a processed image by application of a reconstruction algorithm to the modified detail images and the residual image.

The reconstruction algorithm is illustrated in FIG. 6.

The residual image $g_L$ is first interpolated by interpolator 26 to twice its original size and the interpolated image is next pixelwise added to the detail image of the coarsest level $b'_{L-1}$, using adder 27.

The resulting image is interpolated and added to the next finer detail image. When this process is iterated L times using the unmodified detail images $b_{L-1} \ldots b_0$ then the original image 20 will result. When at the other hand the detail images are modified before reconstruction in accordance with a suitable function then a contrast enhanced image 28 will result. The interpolators 26, 26', 26'', 26''' are identical to those used in the decomposition section.

Reference is again made to FIG. 4 illustrating the data flow.

After reconstruction the image was converted into an image representing logarithm values of exposure values using a logarithmic conversion look up table.

The latitude of the image is normally too large to be printed on film or to be displayed on a monitor. Therefore the latitude was confined to the diagnostically relevant region.

In order to determine the diagnostically relevant region the image histogram was first calculated and then a relevant signal range was selected according to the method described in our European application 546 600; which method is based on an evaluation of the image histogram.

Next the digital data in the selected range were converted into grey values according to an appropriate sensitometric mapping curve that was determined as described in our European application 549 009.

In accordance with the method described in this application a sensitometric mapping curve was created by the steps of defining a canonical monotonical non-constant function $Y(x)$ in an orthogonal coordinate system $(x,y)$ between arbitrary values $x_0$ and $x_1$ and $y_{min}$ and $y_{max}$, determining minimum and maximum density values $D_{smin}$ and $D_{smax}$, determining minimum and maximum signal values $S_{min}$ and $S_{max}$ constituting a range wherein the gradation is defined by the canonical form and outside of which signal values are mapped onto $D_{smin}$ or $D_{smax}$, defining the gradation curve as $$D(s)=D_{smin}+(Y(x(s))-y_{min}).(D_{smax}-D_{smin})/(y_{max}-y_{min})$$

wherein $D(s)$ is the density in the reproduction as a function of the signal value $s$, $x(s)=x_0$ if $s$ is smaller than or equal to $S_{min}$, $x(s)=x_0+(s-S_{min}).(x_1-x_0)/(S_{max}-S_{min})$ if $s$ is comprised between $S_{min}$ and $S_{max}$, and $x(s)=x_1$ if $s$ is larger than or equal to $S_{max}$.

In this embodiment $S_{max}$ was equal to $S_{min}+L$ and $S_{min}= y_0+dy_0+A(y_1+dy_1-y_0-dy_0)-A.L$ wherein L is equal to a predetermined value $L_{min}$ if $L_{min}$ is greater than $y_1+dy_1-y_0-dy_0$ or equal to a predetermined value $L_{max}$ if $L_{max}$ is smaller than $y_1+dy_1-y_0-dy_0$ or L is equal to $y_1+dy_1-y_0-dy_0$ if $y_1+dy_1-y_0-dy_0$ is comprised between $L_{min}$ and $L_{max}$ and wherein A is a constant value between 0 and 1, $dy_0$ and $dy_1$ are offset values comprised between $-L_{max}/2$ and $L_{max}/2$.

Typical values for example for chest radiography are $dy_0=0$; $dy_1=0.1 \log E$, $A=0$, $L_{min}=1.2 \log E$; $L_{max}=1.8 \log E$.

Alternative embodiments are described in the above identified application EP 549 009.

Next, the data were transferred to an output recorder to be printed on film. It was also possible to display the image on a display unit.

In accordance with the present invention the effective sensitivity of the entire read out system is monitored by calculating the noise variance of the read out image and by calculating the ratio of this noise variance to the expected value of the noise variance which was retrieved from a look up table and by thresholding said ratio.

Figure 8:
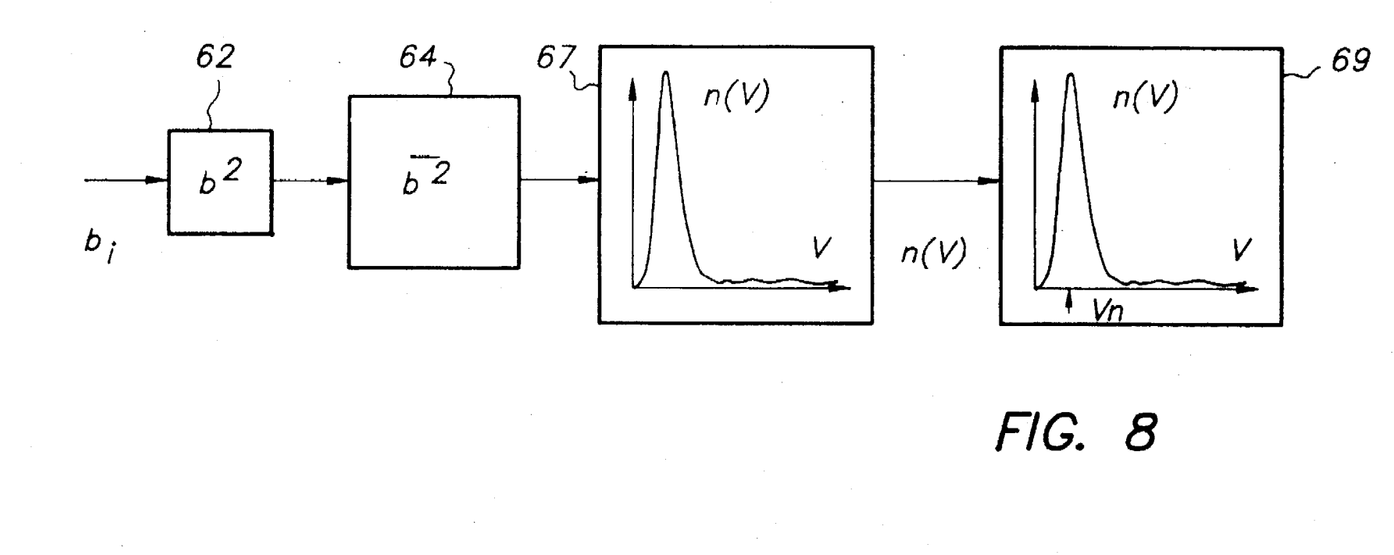
FIG. 8 is a device for calculating the noise variance of the read out image.

FIG. 8 shows a section for calculating the noise variance. The illustrated procedure is especially advantageous in situations wherein one already disposes of a multiresolution representation of the image which was e.g. calculated for the purpose of image enhancing processing.

In the calculation section each detail image $b_i$ resulting from the decomposition of the original image into a sequence of detail images at multiple resolution levels and a residual image is pixelwise transferred to a squaring unit 62, starting with the coarsest detail image. A moving average operator 64 then computes the local variance v at every pixel position by summing all squared pixel values in an N×N neighbourhood centred around the current target pixel (a neighbourhood of 5×5 elements proved to be adequate), and dividing the sum by the number of pixels in the neighbourhood. These local variance values are transferred to a histogram computation unit 67. A histogram is a array, the elements of which are called bins, each bin corresponding with a fixed sampling interval of the signal range associated with the horizontal histogram axis. Each bin resides in a memory cell, all of them being initialised to zero before accepting the first pixel. For each entered variance value the histogram computation unit 67 selects the corresponding bin index and increments the associated bin value by one. After all pixels of a variance image at a particular resolution level have been used this way, the histogram represents the occurrence of every quantised variance value throughout the image.

This local variance histogram is next supplied to a maximum locator 69, which determines the variance value with the highest occurrence $v_n$ in the histogram. This value is used as an estimate for the noise variance within the considered detail image.

In an alternative embodiment each sample of local variance is accounted for updating the histogram only if the pixel value of the original (raw) image at the corresponding position is below a threshold value.

Preferably this threshold value is equal to half the maximum signal value assuming that the signal values are proportional to square root values of the irradiation dose and irradiation doses are situated in the range of sensitivity class values in between class 25 and class 800.

Next a thresholding procedure was applied to the ratio of the effectively calculated noise variance relative to the noise variance retrieved from a look up table.

Figure 7:
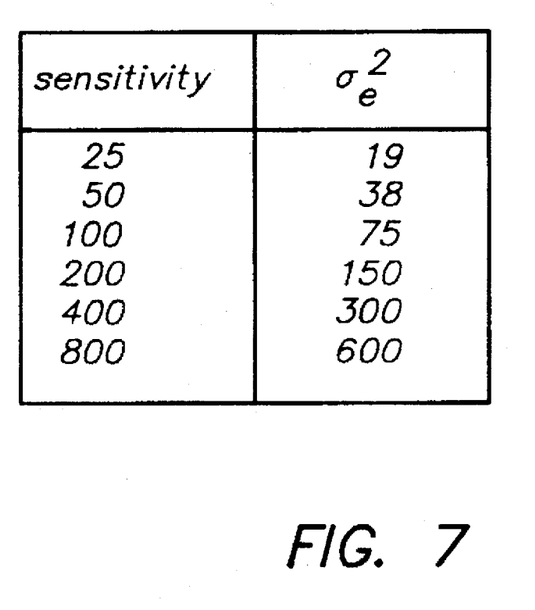
FIG. 7 is a look up table expressing a relation between sensitivity class values and corresponding values of the expected noise variance $\sigma^2_e$.

The values of said look up table were determined in advance following the procedure described hereinbefore. An example of such a look up table is shown in FIG. 7.

The thresholding was performed by comparing the calculated ratio with either of two predetermined threshold values that are representative of the extreme values of a range wherein variance of the sensitivity of the read out system is still acceptable.

A warning signal was generated when the ratio was larger than a, threshold $T_+$ indicating that the sensitivity was too high and a warning signal was also indicated in case the ratio was smaller than $T_-$ indicating that the sensitivity as too small. The warnings were generated in the form of visible indications on the user display of the read out apparatus.

I claim:

1. A method of monitoring the sensitivity of a system for reading a radiation image of an object that has been exposed to irradiation, said radiation image having been stored in a photostimulable phosphor screen, comprising the steps of scanning said screen with stimulating irradiation, detecting the light emitted upon stimulation, converting the detected light into an electric representation, compressing said electric representation through square root amplification, digitizing the compressed electric representation, selecting for a sensitivity class that was set when said radiation image was generated a corresponding expected noise variance value $\sigma_e^2$ from a table which comprises for a number of predefined sensitivity classes corresponding noise variance values, each of said corresponding noise variance values representing the average variance of noise present in an image read out with said system being calibrated for the corresponding sensitivity class, computing for the read out image the effective noise variance $\sigma_y^2$, calculating the ratio $\sigma_y^2/\sigma_e^2$, thresholding said ratio, generating a warning at least in one of the cases wherein said ratio exceeds a threshold value $T_+$ and wherein said ratio is smaller than some threshold value $T_-$.

2. A method according to claim 1 wherein an output is generated of at least one of the result of said thresholding and said ratio.

3. A method according to claim 1 modified in that for a number of successively read out images said ratio is determined to produce a plurality of ratios and that the average value is calculated of said plurality of ratios and that the thresholding step is performed on said average value.

4. A method according to claim 1 modified in that for a number of N successively read out images said ratio is calculated and that a regression line is computed on these ratios, and that in case the absolute value of the slope of said regression line is exceeding a threshold value $T_r$, a warning is generated.

5. A method according to claim 1 wherein said noise variance value is computed by a) establishing a compact neighbourhood centrally around each pixel of said image, computing the local image variance at each center pixel based on the statistics within said neighbourhood, and using said local variance at every pixel to update the corresponding entry of a local variance histogram associated with said image;

b) designating the noise variance of said image as the local variance value that corresponds to the highest number of occurrences within said histogram.

6. A method according to claim 5 wherein said local variance is computed as the average squared value of all pixels within said neighbourhood minus the square average signal value in said neighbourhood.

7. A method according to claim 6 wherein said neighbourhood has an extent of 5×5 pixels.

8. A method according to claim 5 modified in that each sample of local variance is accounted for updating the histogram only if the pixel value of the read out image at the corresponding position is below an established value.

9. A method according to claim 8 wherein the threshold value established in claim 8 is equal to half the maximum of the read out signal values and wherein the irradiation amount to which said object was exposed expressed as a sensitivity class is within the range of 25 to 800.

10. A method according to claim 5 wherein the read out image is decomposed into a set of detail images at multiple resolution levels and a residual image at a resolution level lower than said multiple resolution levels, and wherein said local variance is computed as the average of squared amplitudes of the detailed images obtained by said decomposition.

11. An apparatus for reading a radiation image that has been stored in a photostimulable phosphor screen comprising means for scanning said screen with stimulating irradiation, read out means for detecting light emitted upon stimulation and for converting said light into an electric signal representation, amplifying means having a square root characteristic for amplifying said signal representation, means for storing a table which comprises for a number of predefined sensitivity class settings corresponding noise values $\sigma^2_{e,i}$, each of said noise variance values representing the average variance of noise present in an image read out with read out means being calibrated for the corresponding sensitivity class, means for retrieving from said table for a given sensitivity class the corresponding noise value $\sigma^2_e$, means for calibrating said read out means for a specific sensitivity class, means for reading an image stored in a screen, means for computing for said read out image the effective noise variance $\sigma^2_y$, means for calculating the ratio $\sigma^2_y/\sigma^2e$, means for thresholding said ratio, means for generating a warning at least in one of the cases wherein said ratio exceeds a threshold value $T_+$ and wherein said ratio is smaller than some threshold value $T_-$.

12. An apparatus according to claim 11 provided with means for outputting at least one of said ratio and the result of said thresholding.

* * * * *